(12) United States Patent
Schoisswohl et al.

(10) Patent No.: US 7,454,048 B2
(45) Date of Patent: *Nov. 18, 2008

(54) METHODS AND SYSTEMS FOR MOTION CORRECTION IN AN ULTRASOUND VOLUMETRIC DATA SET

(75) Inventors: Armin Schoisswohl, Wels (AT); Peter Falkensammer, Vocklabruck (AT)

(73) Assignee: General Electric Company, Schenectady, NY (US)

( * ) Notice: Subject to any disclaimer, the term of this patent is extended or adjusted under 35 U.S.C. 154(b) by 858 days.

This patent is subject to a terminal disclaimer.

(21) Appl. No.: 10/928,938

(22) Filed: Aug. 27, 2004

(65) Prior Publication Data

US 2006/0045318 A1    Mar. 2, 2006

(51) Int. Cl.
*G06K 9/00* (2006.01)
(52) U.S. Cl. ..................................... 382/131; 382/128
(58) Field of Classification Search ................ 382/128, 382/131, 275; 600/413; 378/62
See application file for complete search history.

(56) References Cited

U.S. PATENT DOCUMENTS

| | | | |
|---|---|---|---|
| 5,582,173 A | 12/1996 | Li | |
| 5,615,677 A * | 4/1997 | Pelc et al. | 600/410 |
| 5,655,535 A * | 8/1997 | Friemel et al. | 600/443 |
| 5,806,521 A * | 9/1998 | Morimoto et al. | 600/447 |
| 5,876,342 A | 3/1999 | Chen et al. | |
| 5,899,861 A * | 5/1999 | Friemel et al. | 600/443 |
| 6,162,174 A | 12/2000 | Friemel | |
| 6,254,539 B1 | 7/2001 | Pang et al. | |
| 6,283,917 B1 | 9/2001 | Jago et al. | |
| 6,464,643 B1 | 10/2002 | Brock-Fisher | |
| 6,527,717 B1 | 3/2003 | Jackson et al. | |
| 6,980,844 B2 * | 12/2005 | Schoisswohl | 600/407 |
| 2002/0025017 A1 | 2/2002 | Stergiopoulous et al. | |
| 2003/0158483 A1 | 8/2003 | Jackson et al. | |
| 2004/0136490 A1 | 7/2004 | Edic et al. | |
| 2004/0167395 A1 | 8/2004 | Behrenbruch et al. | |
| 2005/0002550 A1 * | 1/2005 | Jabri et al. | 382/131 |

* cited by examiner

*Primary Examiner*—Duy M Dang
(74) *Attorney, Agent, or Firm*—The Small Patent Law Group; Dean D. Small (57) ABSTRACT

A method for correcting motion artifacts within a volumetric data set is provided. The method includes obtaining a volumetric data set containing spatial and temporal information regarding an object. The volumetric data set is organized into data slices such that at least two adjacent data slices are representative of a common physical slice within the object at different points in time. The relative motion between adjacent data slices in determined for the slices of the volumetric data set and used to correct for the relative motion between said adjacent slices.

22 Claims, 8 Drawing Sheets

METHODS AND SYSTEMS FOR MOTION CORRECTION IN AN ULTRASOUND VOLUMETRIC DATA SET

BACKGROUND OF THE INVENTION

The present invention relates to motion correction in diagnostic ultrasound. In particular, the present invention relates to methods and apparatus for acquiring and processing ultrasound data to reduce motion artifacts of ultrasound images.

At least some known ultrasound systems are capable of spatially compounding a plurality of ultrasound images of a given target into a compound image. The term "compounding" as used throughout means combining multiple data sets, each of which defines an image frame, non-coherently to create a new, single data set. The data sets may be obtained at different locations and/or may each be obtained at different times. The data sets or frames are combined to generate a single compound image by combining the corresponding data from each point in the compound image target. Real time spatial compound imaging may be performed by acquiring a series of partially overlapping component image frames from substantially independent locations. The component frames are combined into a compound image by estimating the location change, correcting for the estimated change and subsequently combining by summation, averaging, peak detection, or other combinational means. The compounded image may display a wider field of view.

In real time spatial compound imaging, several image frames are needed to produce each new compound image frame. A time difference exists between acquisition of the first frame used in constructing the compound image and the last frame used in the compound image. Significant image misregistration may exist due to the time difference between the acquisition of frames. The image misregistration may result in compound image blurring if a large number of image frames are used to construct the compound image. Relatively less blurring may result if a smaller number of image frames are used to construct the image. While it is generally desirable to acquire a large number of image frames, the large number of image frames requires a longer period of time for acquisition, during which blurring may increase to an undesirable level.

There are certain types of motion of the image target that are of interest, for example, the motion of a beating heart. However, undesirable motion also exists. Examples of causes for undesirable motion are the breathing of the patient being scanned, the movement of a fetus in a patient thus causing undesired movement of the image target, and undesirable movement of the ultrasound scanner by the operator. A need exists for improved methods and systems for motion correction in volumetric data sets.

BRIEF DESCRIPTION OF THE INVENTION

In one embodiment, a method for correcting motion artifacts within a volumetric data set is provided. The method includes obtaining a volumetric data set containing spatial and temporal information regarding an object. The volumetric data set is organized into data slices such that at least two adjacent data slices are representative of a common physical slice within the object at different points in time. The relative motion between adjacent data slices is determined for the slices of the volumetric data set and used to correct the relative positions of the adjacent slices.

In another embodiment, an ultrasound system is provided that corrects motion artifacts within a volumetric data set. The system includes a memory for storing a volumetric data set containing spatial and temporal information regarding an object. The volumetric data set is organized into data slices whereby at least two adjacent data slices are representative of a common physical slice within the object at different points in time. A processing unit is included to determine relative motion between adjacent data slices in the volumetric data set. The processing unit corrects for the relative motion between adjacent first and second slices.

DETAILED DESCRIPTION OF THE INVENTION

Figure 1:
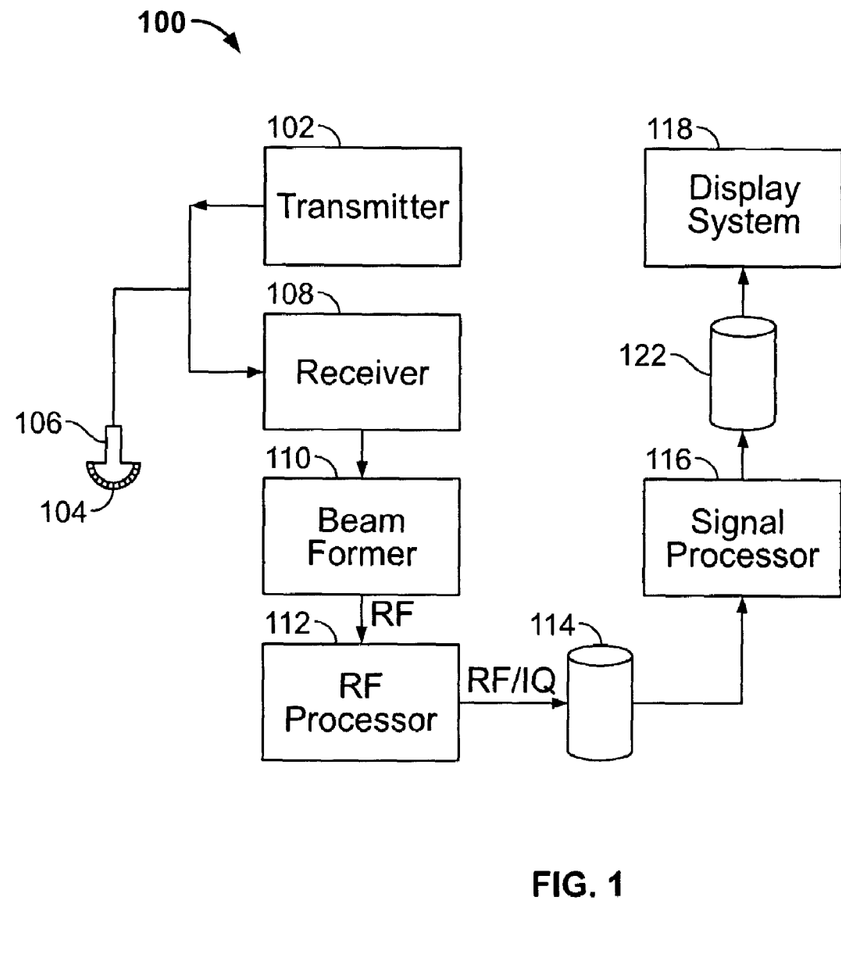
FIG. 1 is a block diagram of an ultrasound system formed in accordance with an embodiment of the present invention.

FIG. 1 is a block diagram of an ultrasound system 100 formed in accordance with an embodiment of the present invention. The ultrasound system 100 includes a transmitter 102 that drives a plurality of transducer elements 104 within an array transducer 106 to emit pulsed ultrasound signals into a body. A variety of geometries may be used. The ultrasound signals are back-scattered from density interfaces and/or structures in the body, like blood cells or muscular tissue, to produce echoes which return to the transducer elements 104. A receiver 108 receives the echoes. The received echoes are passed through a beamformer 110, which performs beamforming and outputs a RF signal. The RF signal then passes through a RF processor 112. Alternatively, the RF processor 112 may include a complex demodulator (not shown) that demodulates the RF signal to form IQ data pairs representative of the echo signals. The RF or IQ signal data may then be routed directly to an RF/IQ buffer 114 for temporary storage.

The ultrasound system 100 also includes a signal processor 116 to process the acquired ultrasound information (i.e., RF signal data or IQ data pairs) and prepare frames of ultrasound information for display on a display system 118. The signal processor 116 is adapted to perform one or more processing operations according to a plurality of selectable ultrasound modalities on the acquired ultrasound information. In the exemplary embodiment, acquired ultrasound information is processed in real-time during a scanning session as the echo signals are received. In an alternative embodiment, the ultrasound information may be stored temporarily in the RF/IQ buffer 114 during a scanning session and processed in less than real-time in a live or off-line operation.

The ultrasound system 100 may continuously acquire ultrasound information at a frame rate that exceeds fifty frames per second, which is approximately the perception rate of the human eye. The acquired ultrasound information may be displayed on the display system 118 at a slower frame-rate. An image buffer 122 is included for storing processed frames of acquired ultrasound information that are not scheduled to be displayed immediately. In the exemplary embodiment, the image buffer 122 is of sufficient capacity to store at least several seconds worth of frames of ultrasound information. The frames of ultrasound information are stored in a manner to facilitate retrieval thereof according to its order or time of acquisition. The image buffer 122 may include at least one memory device, such as, but not limited to, a random access memory (RAM) or other known data storage medium.

Figure 2:
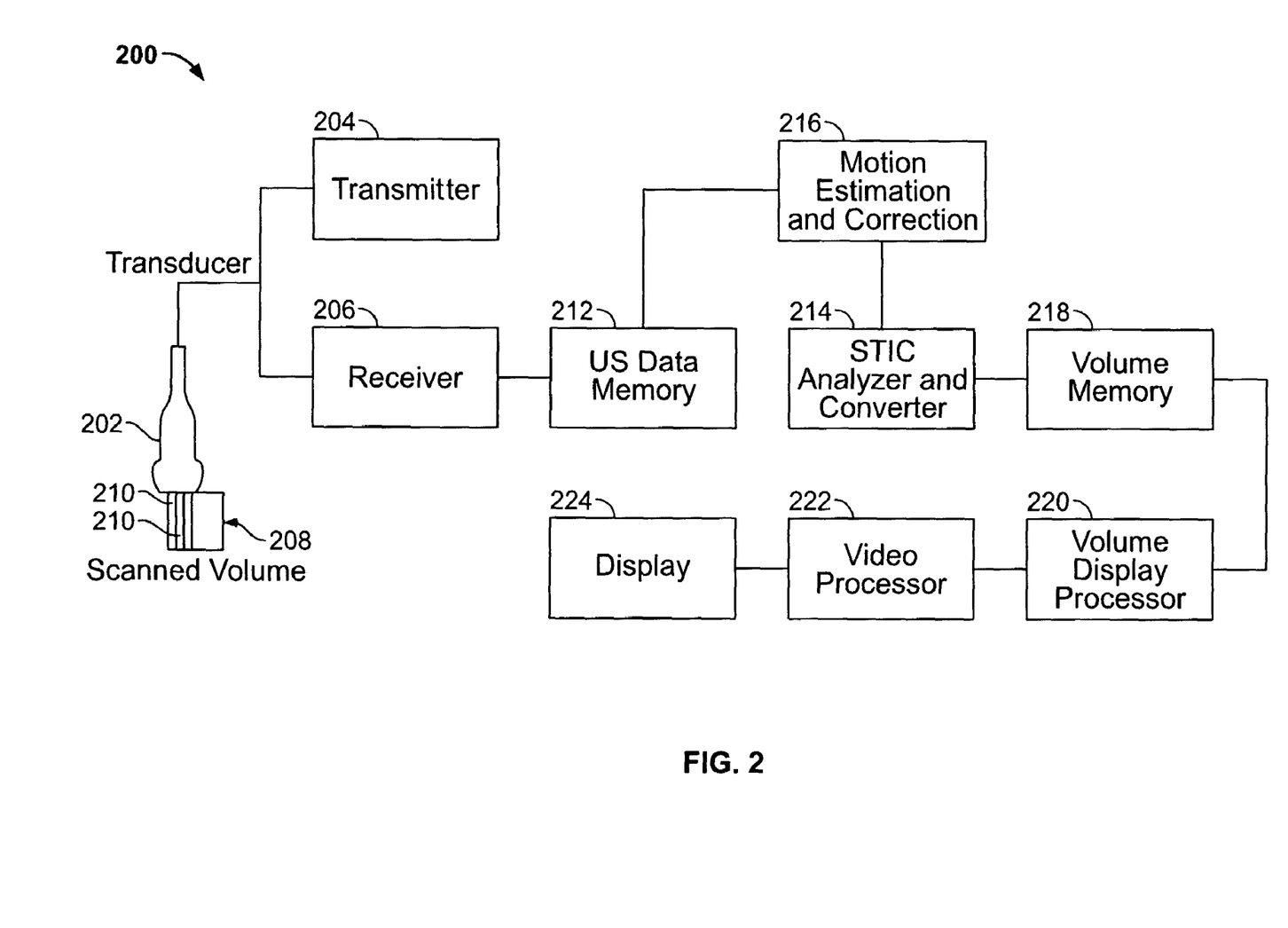
FIG. 2 is a block diagram of an ultrasound system used to acquire and process ultrasound images formed in accordance with an embodiment of the present invention.

FIG. 2 illustrates an ultrasound system 200 formed in accordance with an embodiment of the present invention. The system 200 includes a probe 202 connected to a transmitter 204 and a receiver 206. The probe 202 transmits ultrasonic pulses and receives echoes from structures inside of a scanned ultrasound volume 208. Memory 212 stores ultrasound data from the receiver 206 derived from the scanned ultrasound volume 208. The volume 208 may be obtained by various techniques (e.g., 3D scanning, real-time 3D imaging, volume scanning, 2D scanning with transducers having positioning sensors, freehand scanning using a Voxel correlation technique, 2D or matrix array transducers and the like).

The probe 202 is moved, such as along a linear or arcuate path, while scanning a region of interest (ROI). At each linear or arcuate position, the probe 202 obtains scan planes 210. The scan planes 210 are stored in the memory 212, and then passed to a spatial and temporal image correlation (STIC) analyzer and converter 214. In some embodiments, the probe 202 may obtain lines instead of the scan planes 210, and the memory 212 may store lines obtained by the probe 202 rather than the scan planes 210. Data output is passed from the memory 212 through a motion estimator/corrector 216 and then to the STIC analyzer and converter 214. The STIC analyzer and converter 214 stores data in a volume memory 218 and the data is accessed by a volume display processor 220. The volume display processor 220 performs volume rendering and/or other image processing techniques upon the data. The output of the volume display processor 220 is passed to a video processor 222 and from the video processor 222 to a display 224.

The position of each echo signal sample (Voxel) may be defined in terms of geometrical accuracy (i.e., the distance from one Voxel to the next), ultrasonic response, and derived values from the ultrasonic response. Suitable ultrasonic responses may include B-mode, gray scale values, color flow values, and angioDoppler or power Doppler information.

Figure 3:
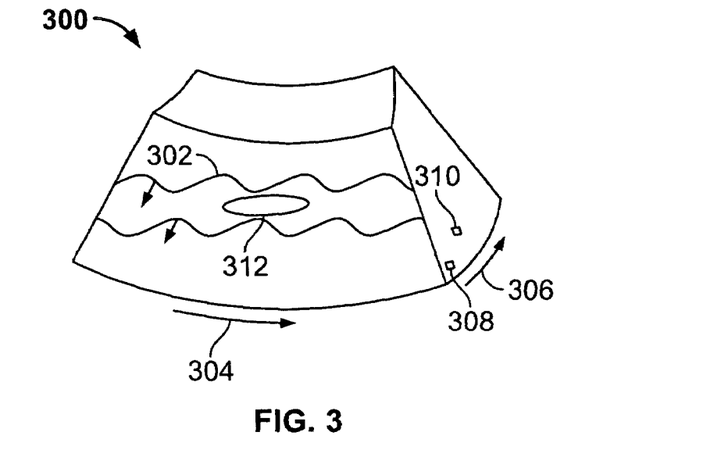
FIG. 3 illustrates an exemplary scan of an object acquired by the ultrasound system shown in FIG. 1.

In the illustration of FIG. 3, the array transducer 106 (FIG. 1) may scan a volume 300 containing an object 312 slowly, for example, one volumetric sweep (e.g., a 10-30 degree sweep) of the object 312 within 7 to 15 seconds. A volumetric sweep may be produced by emitting ultrasound waves 302 along a slice 304 of the volume 300 and then obtaining a next slice 304 by varying the elevation 306 of the ultrasound scan. For example, the voxel 308 may be in one volumetric slice 304 and yet another voxel 310 may be in a different volumetric slice 304. During the sweep, the object 312 may change shape due to motion of the object 312, such as a beating heart. Undesirable motion artifacts may also result in the volumetric data set of the sweep due to motion of the array transducer 106. For example, breathing by the scanned patient may cause movement of the array transducer 106, as well as other causes previously discussed herein.

Figure 4:
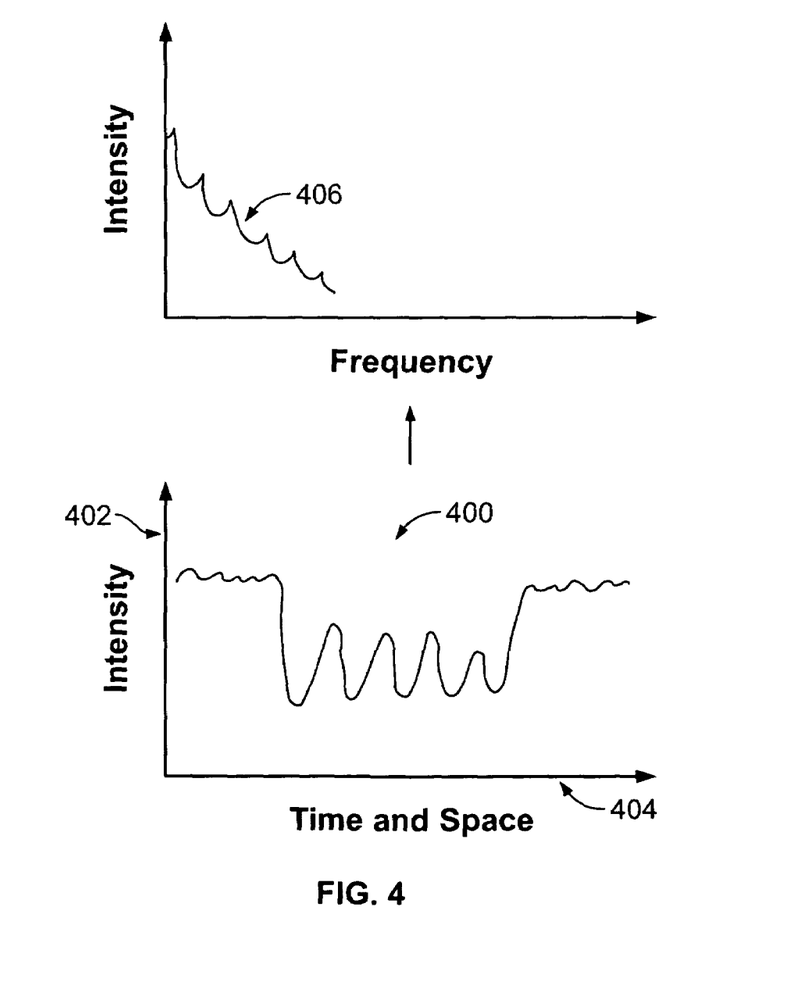
FIG. 4 is an exemplary graph of intensity versus time and space (T/S) axis for scan data collected by the ultrasound system of FIG. 1.

FIG. 4 is an exemplary graph 400 illustrating intensity 402 versus a time and space (T/S) axis 404 for scan data collected by the system 100 (FIG. 1). A first part of the method for correcting motion artifacts within a volumetric data set (VDS) includes obtaining a VDS containing spatial and temporal information regarding an object 312 (FIG. 3). The intensity 402 may be from volumetric data for a scan line point. A method (e.g., fast Fourier transform) may be applied to the intensity 402 to produce a frequency spectrum 406. In the case of the object 312 being a heart, the frequency spectrum 406 produced includes a frequency spectrum of the tissue signal superimposed with the motion of the heart beat. Further, the frequency spectrum 406 may include undesirable motion superimposed as well as motion related to the heart beat. Undesirable motion may have the greater effect contributing to differences between two adjacent slices of the VDS. For example, the change in the shape of the heart between two adjacent slices may be very minimal and, undesirable motion, if present, may be the predominant contributor to image misregistration. Adjacent slices may be moved (translated and rotated) with respect to one another to attempt matching the slices, for example, matching on the intensities of the slices. The movement required for a best match of the adjacent slices may be recorded as a relative motion (translation and rotation change) of one slice to the other.

Figure 5:
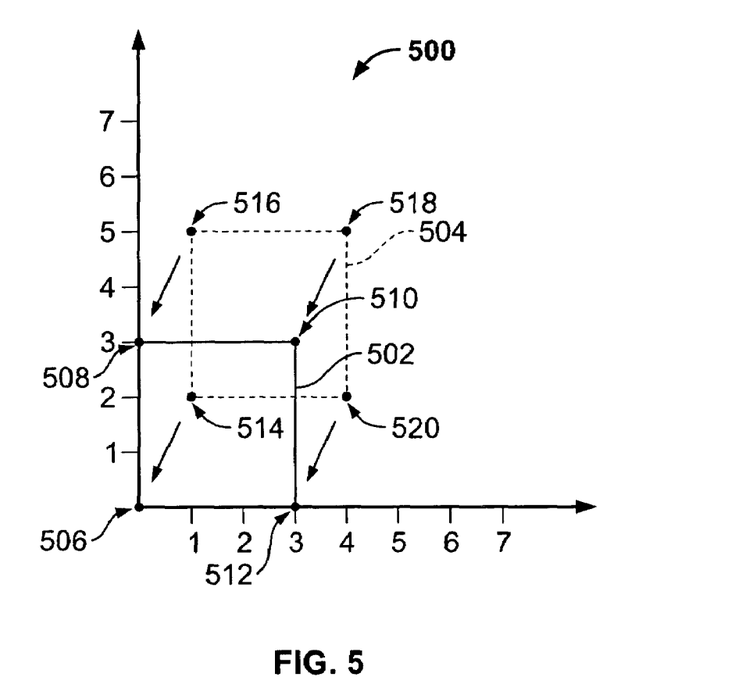
FIG. 5 is an example in a Cartesian coordinate system for matching two images translated relative to one another.

FIG. 5 illustrates a portion 500 of a volumetric data set in which adjacent data slices 502 and 504 are translated from one another in the Cartesian coordinate system. The data slices 502 and 504 are moved or displaced relative to one another in the x-y plane. Point 514 in data slice 504 is displaced 1 unit to the right in the x-direction and 2 units upwards in the y-direction from the corresponding point 506 in the data slice 502. Likewise, points 516, 518, and 520 in data slice 504 are displaced by corresponding amounts in the x and y-directions from the corresponding points 508, 510, and 512 in adjacent data slice 502. By adding relative changes or deltas ($\Delta$) in the x and y coordinates, e.g., $\Delta x=-1$ and $\Delta y=-2$ to any point of data slice 504, the point is moved to its corresponding/correlated point in data slice 502. For example, if relative changes $\Delta x=-1$ and $\Delta y=-2$ are added to point 518 having coordinates (4,5), the coordinates (4−1=3, 5−2=3) or (3,3) are obtained for the corresponding point 510 of data slice 502.

Figure 6:
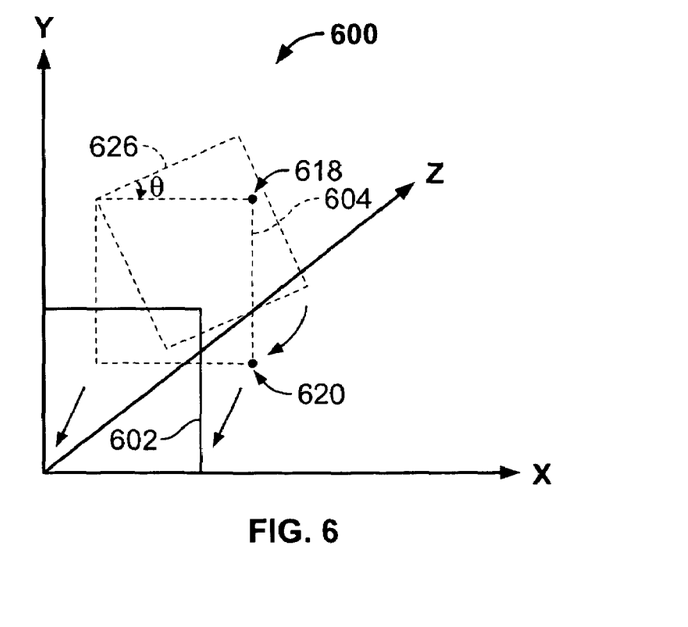
FIG. 6 is an example in a Cartesian coordinate system for matching two images translated and rotated relative to one another.

FIG. 6 illustrates a portion 600 of the VDS in which adjacent data slices 602 and 604 are rotated and translated from one another. In the example of FIG. 6, the segment connecting points 618 and 620 of data slice 604 has been rotated an angular amount $\theta$ in the x-y plane. Thus, the data slice 602 may be obtained from data slice 626 by rotating the data slice 626 and translating the resulting data slice 604 to obtain data slice 602. Alternatively, data slice 626 may be rotated, then translated (e.g., in the x-direction), rotated again, and translated again (e.g., in the y-direction) to obtained the final result of data slice 602. Alternatively, data slice 602 may be obtained from data slice 626 by first translating data slice 626 and then rotating the result to obtain data slice 602. The order of operations of rotating and translating may vary. The examples of FIGS. 5 and 6 show how image matching, also known as registration, may be done to obtain one image, e.g., data slice 602, from another, e.g., data slice 626.

Various registration algorithms may be used to perform image correlation, for example, registration algorithms that make use of geometrical features in the images such as points, lines and surfaces, determine the transformation by identifying features such as sets of image points that correspond to the same physical entity visible in both frames. Registration algorithms may be based on image intensity values such that they determine an image transformation that optimizes a similarity measure between each slice. Registration algorithms may also reduce the amount of search in a search space (e.g., the number of combinations of translations and rotations to perform on one data set to obtain a best match for another).

A volumetric data set containing spatial and temporal information regarding an object is collected in real-time from the ultrasound scan. The raw volumetric data is organized into data slices and stored in memory, for example the memory 202 of system 200 of FIG. 2. Any two adjacent slices are representative of a common physical slice within the scanned object at different points in time. Once a VDS has been obtained a difference is calculated in position (translation) and orientation (rotation) between adjacent data slices, herein referred to as relative motion of the adjacent slices. A processing unit, e.g., the scan converter 206 of FIG. 2, may be used to perform the calculations. The relative motion calculation is done between consecutive adjacent slices, e.g., between a first and second slice, between a second and third slice, between a third and fourth slice, and so forth. The relative motion calculations are comparative to the operations discussed in FIGS. 5 and 6. The VDS may be mapped from an acquisition coordinate system, e.g., a polar coordinate system, for the acquired VDS into a rectangular coordinate system, e.g., a Cartesian coordinate system, before performing relative motion calculations. Once the relative motion has been recorded between adjacent slices for all adjacent slices, the volumetric raw data may then be corrected for the relative motion through a series of operations. The relative motion calculations may be recorded between adjacent slices in a change notation, e.g., $\Delta x$ being a change in the x-axis direction, $\Delta y$ being a change in the y-axis direction, and $\Delta \theta$ being the rotation angle within the x-y. Thus, ($\Delta x(21)$, $\Delta y(21)$, $\Delta \theta(21)$) may designate the change between slices 2 and 1 with respect to slice 1, ($\Delta x(32)$, $\Delta y(32)$, $\Delta \theta(32)$) may designate the change between slices 3 and 2 with respect to slice 2, and so forth.

Correcting the volumetric raw data for the relative motion between adjacent slices includes the following operations, to be described in detail following herein. Using the calculated relative motions, compute a cumulative absolute motion of each data slice with respect to a reference coordinate system (RCS), e.g., the RCS wherein a first slice has no change. The reference coordinate system (RCS) for a first slice may result from a simple conversion to Cartesian coordinates of the acquisition coordinate system slice coordinates, which may be in a polar coordinate system. Based on the absolute motion of the data slices with respect to the RCS, define a more optimal or correct RCS (CRCS). Even though the RCS may be a Cartesian coordinate system, the resulting CRCS may not be. Once defining the CRCS, move/map a sampling sector or slice, e.g., a sampling scan line with sampling points identified, from the RCS to the new CRCS.

Generate an increased density of sampling points in the new CRCS by an interpolation method (e.g., doubling or tripling the line density of the sampling scan line). Using the generated density, search and find/extract (e.g., reverse map) the density of sampling points in the CRCS to correlated VDS points in the RCS. Identify the translation/rotation motion that maps the correlated VDS points from the RCS to the corresponding density of sampling points in the CRCS. Apply the identified translation/rotation to all the VDS data slices of the acquisition coordinate system. The motion estimator/corrector 216 of FIG. 2 may, for example, perform the above operations, then storing the translated/rotated raw volumetric data in slice memory 210. Once completing the above described operations, the raw motion corrected volumetric data may then be processed to form an ultrasound image.

Alternatively, the calculation of relative motion and adjusting the data slices for motion may be done after some processing (compounding) of the raw data, but current real-time computational performance may prevent performing the operations of the described method in an alternative sequence with the image compounding.

Figure 7:
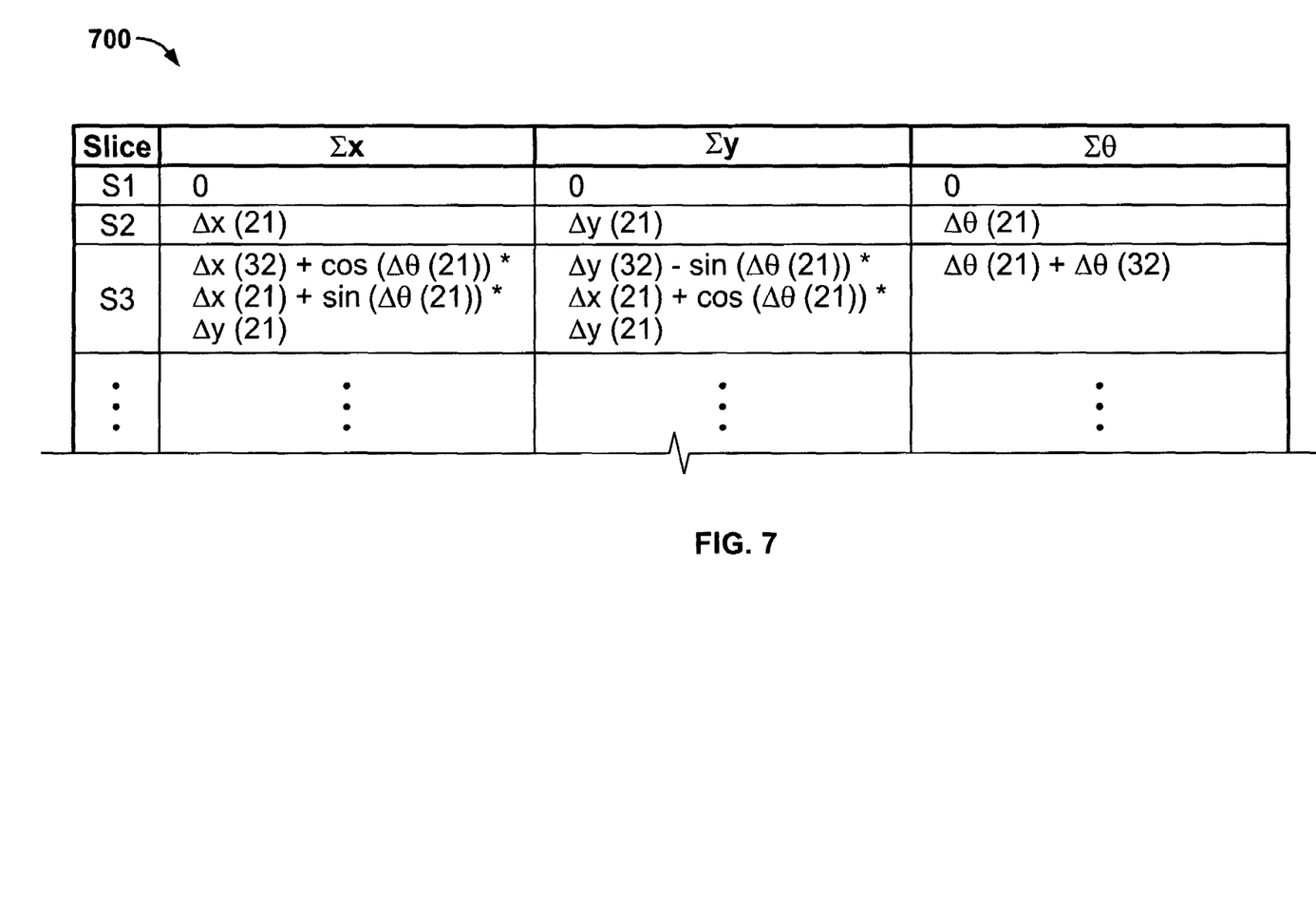
FIG. 7 is an example of a cumulative table with cumulative/absolute motions recorded for VDS data collected by the ultrasound system of FIG. 1.

FIG. 7 shows a cumulative table 700 with cumulative/absolute motions for the VDS slices calculated. The cumulative absolute motion of the data set slices with respect to a reference coordinate system (RCS) may be determined by cumulatively adding the relative motions of adjacent slices with respect to a reference slice/reference system, as shown in cumulative table 700. As an example, in the RCS wherein the first slice S1 has no change, $\Delta x=0$, $\Delta y=0$, and $\Delta \theta=0$. A second slice S2 may have an absolute motion change equivalent to the relative motion change between slices 2 and 1, e.g., the relative motion change being ($\Delta x(21)$, $\Delta y(21)$, $\Delta \theta(21)$). This notation may be read as the relative change in x for slice 2 with respect to slice 1, the relative change in y for slice 2 with respect to slice 1, and the relative change in rotation $\theta$ for slice 2 with respect to slice 1. The absolute motion change for a third slice S3 may be determined by adding to the determined relative motion change for slice 3 with respect to slice 2 the rotated absolute motion change of slice 2. For example, the absolute motion change for S3 is ($\Delta x(32)+\cos(\Delta\theta(21))*\Delta x(21)+\sin(\Delta\theta(21))*\Delta y(21)$, $\Delta y(32)-\sin(\Delta\theta(21))*\Delta x(21)+\cos(\Delta\theta(21))*\Delta y(21)$, $\Delta\theta(21)+\Delta\theta(32)$). In similar fashion, the absolute motion change in succeeding slices may be calculated. The computation of absolute motion requires knowing the motion of all the volumetric data slices, as compared to only knowing two adjacent data slices for relative motion computation.

Figure 8:
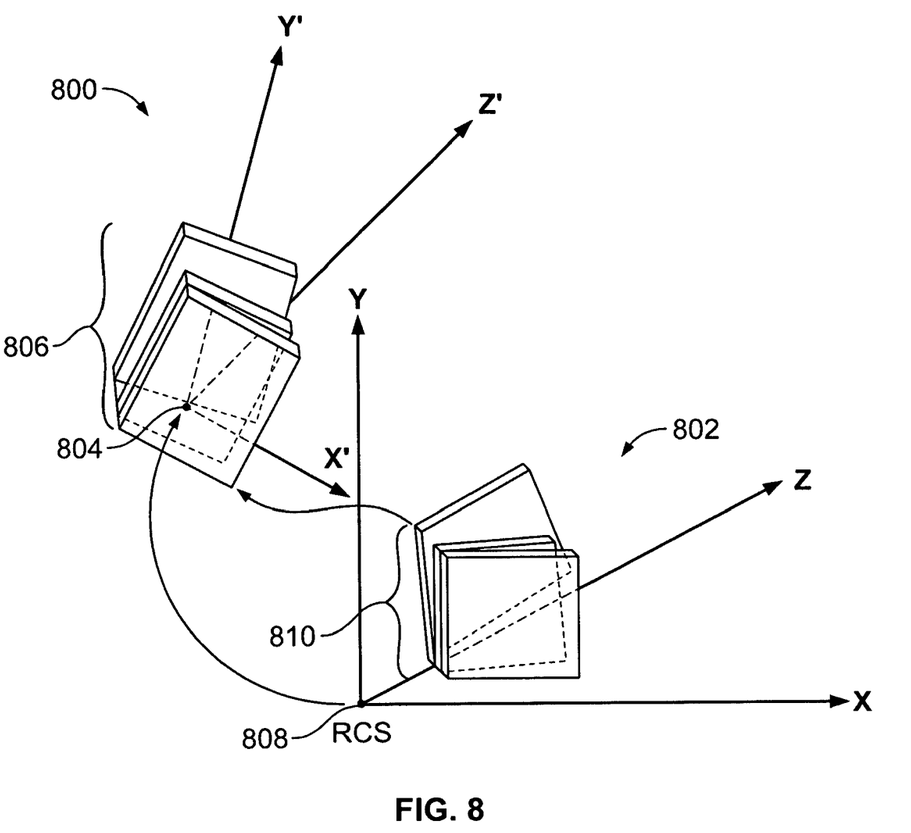
FIG. 8 is an example of how the VDS data is mapped from an original to a corrected reference coordinate system (CRCS).

FIG. 8 illustrates a CRCS 800. Based on the absolute motion of the data set slices with respect to an RCS 802, e.g., the absolute motion exemplified in the table 700, a corrected reference coordinate system CRCS 800 is determined such that the volumetric slices of data become more centered around the origin point 804 of the CRCS 800. The CRCS 800 may be chosen with an origin 804 so as to provide some of the best overlap of the volumetric data whereby each data slice would be moved minimally if the slice were to be moved/positioned in the CRCS 800. The CRCS origin 804 may be determined, for example, by averaging the minimum and maximum shift in the translation/rotation or by assuming the mid-point value in the translation/rotation shifts, or by deleting the ends of shift in volumetric data and applying some form of data reduction. By selecting the CRCS 800 whereby the volumetric data slices would be centered if moved from the RCS 802 to the CRCS 800, a lesser amount of volumetric data is needed to obtain a quality image. A CRCS optimally chosen may help prevent cutting data (removing data) from one end of the data range more than from another end. The CRCS 800 of FIG. 8 may not be a rectangular or Cartesian coordinate system, although the RCS 802 may be. Also, the RCS 802 may be the result of converting original volumetric data from polar coordinates to a Cartesian coordinate system for the purpose of determining the relative translation/rotation between adjacent slices. The Cartesian RCS 802 resulting from a polar coordinate system conversion may be accurate enough for determining relative motion estimations, but not accurate enough for image resolution. Thus, it may be desirable to motion correct the data slices in the original acquisition coordinate system (e.g., polar coordinate system) for motion artifacts.

Figure 9:
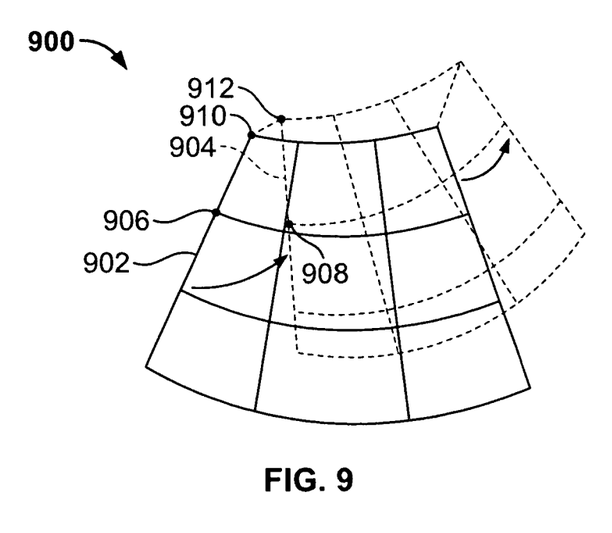
FIG. 9 is an example of scan line data samples mapped from a reference coordinate system (RCS) to a corrected RCS (CRCS) for scan data collected by the ultrasound system of FIG. 1.

FIG. 9 illustrates an example of a mapping 900 of scan line data samples from the RCS 802 to the CRCS 800. The sampling points 906 and 910 of scan line 902 are mapped into corresponding sampling points 908 and 912 of scan line 904. The translation/rotation that is applied to determine the CRCS 800 from the RCS 802 is applied to map the scan line 902 into the scan line 904.

Figure 10:
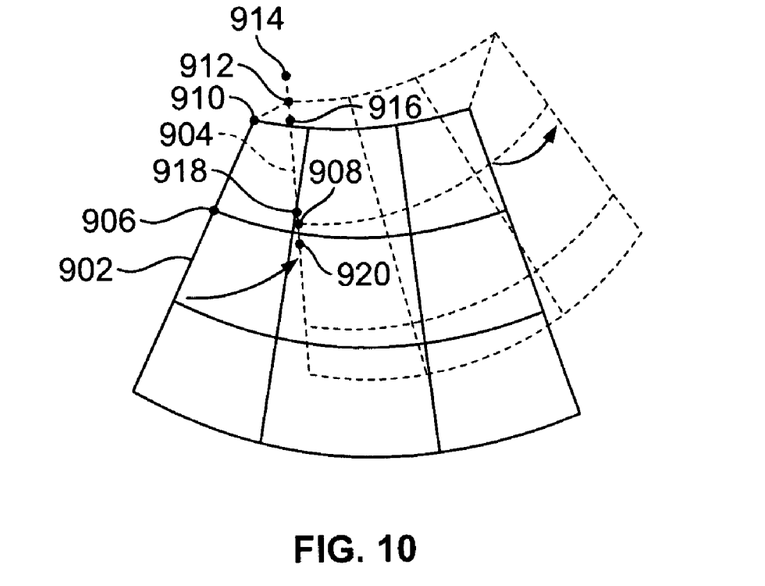
FIG. 10 is an example of how the number of sampling points are increased for the mapping operation of FIG. 9.

FIG. 10 illustrates an example of increasing the number of sampling points for the mapping of FIG. 9. Through various techniques, e.g. interpolation, an increase in the density of the sampling points along the scan line 904 may be produced (e.g. doubling or tripling the sample points originally mapped). The increase in the number of sampling points along the scan line 904, e.g. the additions of sampling points 914, 916, 918, and 920, may be used to better determine a re-positioning of RCS 802 sampling points, e.g. sampling points 906 and 910. Once a greater density of sampling points (e.g. sampling points 908, 912, 914, 916, 918, and 920) has been created for the scan line 904 within the CRCS 800, the greater density of sampling points may be reverse mapped/correlated to matching VDS data within the RCS 802. The correlation of the sampling points in the CRCS 800 (e.g. 908, 912, 914, 916, 918, and 920) to matching sampling points within the actual volumetric data identifies a relative motion (translation/rotation) that may be applied to map the correlated RCS 802 sampling points into the CRCS 800 sampling points.

Figure 11:
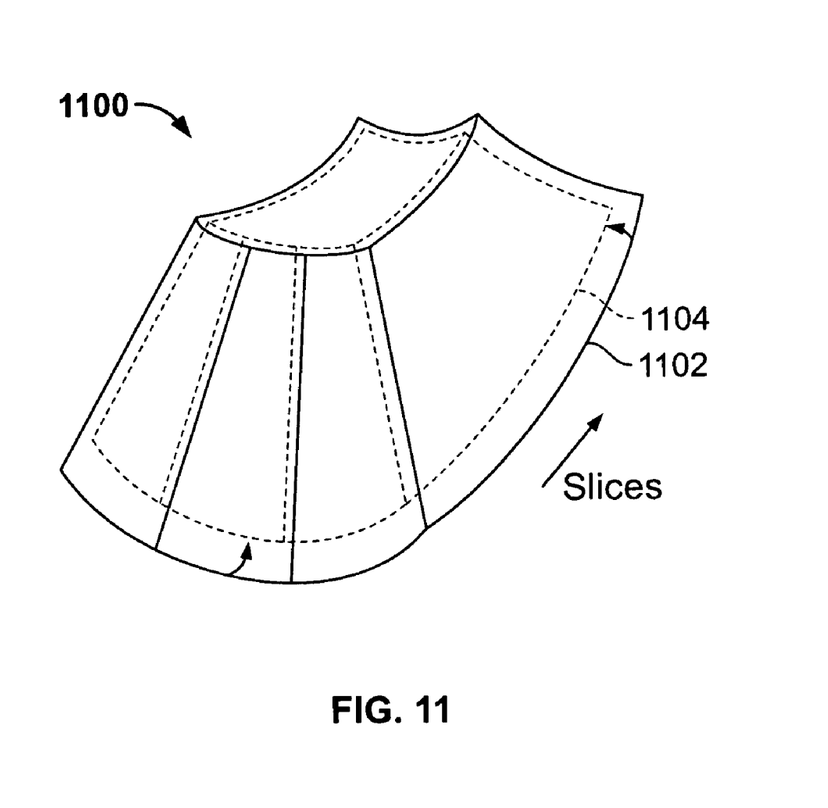
FIG. 11 is an example of a motion correction for the VDS data slices collected by the ultrasound system of FIG. 1.

FIG. 11 illustrates a motion correction 1100 for the VDS data slices. The motion correction 1100 may be accomplished by applying the identified relative motion that maps sampling points from the RCS 802 to the correlated sampling points in the CRCS 800. The identified relative motion may be applied to all data points/slices 1102 of the VDS as located within the acquisition reference coordinate system to produce motion corrected slices 1104. Thus, the identified relative motion may first be adjusted for application in the acquisition reference coordinate system, e.g., a polar coordinate system, before application to the VDS data. Applying the identified relative motion to all VDS data slices 1102 in the acquisition coordinate system results in a VDS adjusted for motion artifacts, e.g., motion corrected slices 1104. In this way, some blurring of the ultrasound image due to motion artifacts may be factored out of the VDS data.

Figure 12:
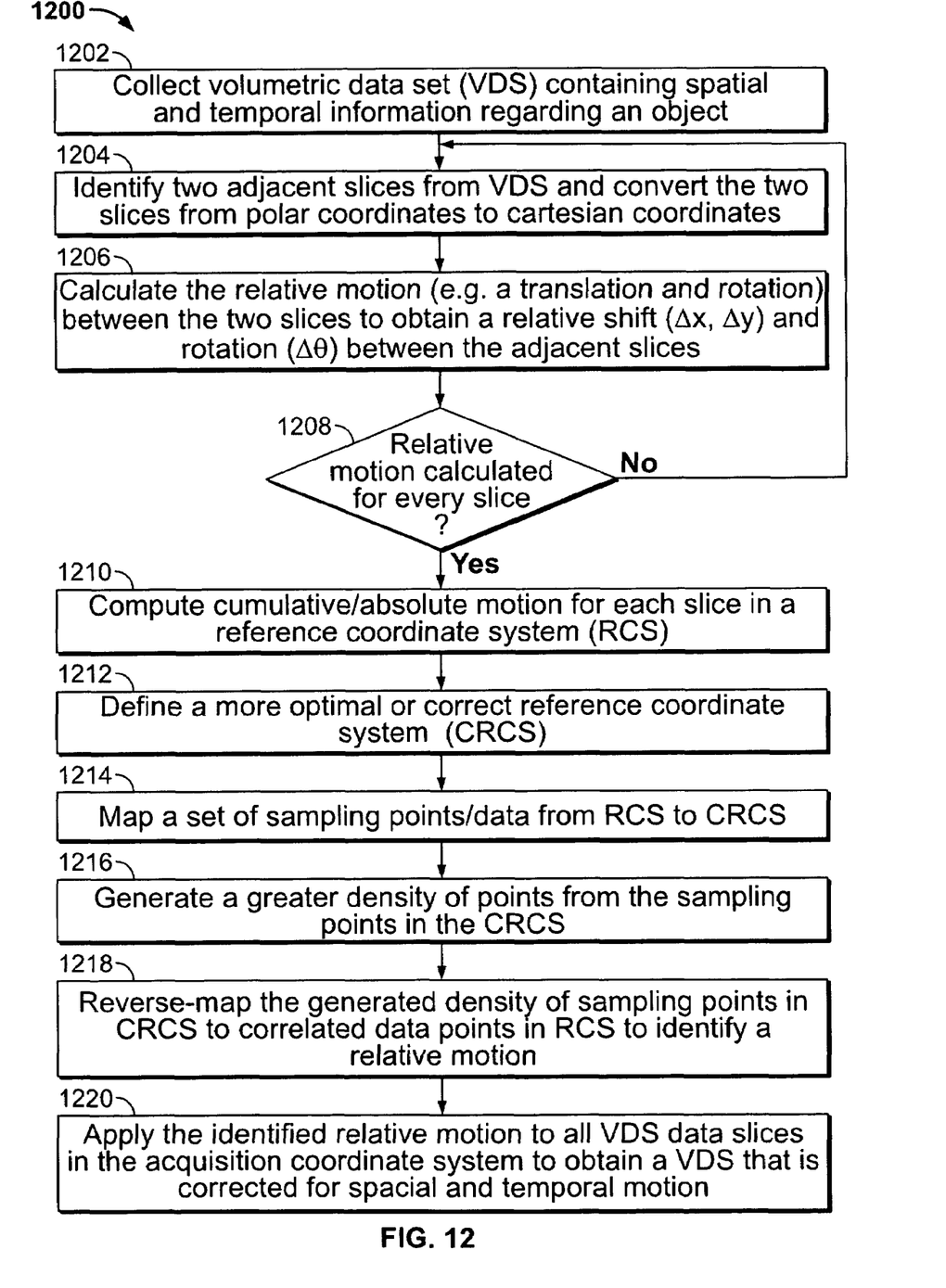
FIG. 12 is a flowchart of an exemplary method for correcting for motion in ultrasound scan data.

FIG. 12 is a flowchart 1200 of an exemplary method for correcting for motion in ultrasound scan data. Volumetric scan data (VDS) that may contain spatial and temporal information is collected 1202, e.g., by the ultrasound system 200 of FIG. 2. Adjacent slices are identified 1204 within the VDS and converted 1204 from polar coordinates to Cartesian coordinates. Relative motion is then calculated 1206 between two adjacent slices to obtain a relative motion (shift/translation (e.g., Δx, Δy) and rotation (e.g., Δθ)) between the adjacent slices. For example, translation and rotation may be calculated between the adjacent data slices 602 and 604 of FIG. 6. Step 1204 and 1206 can alternatively be combined in one step. A determination is made at 1208 as to whether additional adjacent slices exist for calculation of relative motion. If so, identification 1204 and conversion 1204 of adjacent slices and further calculation 1206 of relative motion is performed for the additional adjacent slices. Once relative motion calculations are made for all adjacent slices, the cumulative/absolute motion for each slice in a chosen reference coordinate system (RCS) is computed 1210. The resulting computation may be stored, for example, in the cumulative table 700 shown in FIG. 7. With the cumulative/absolute motion available for each slice, a CRCS is defined 1212 that offers a more centered view of the VDS data. For example, the data slices 806 illustrated in FIG. 8 appear more centered about the CRCS origin 804, in comparison to the positioning of the data slices 810 relative to the RCS origin 808. Sampling points/slices defined within the RCS are mapped 1214 to locations within the CRCS reference. FIG. 9, for example, shows the sample points 906 and 910 mapped from an RCS to points 908 and 912, correspondingly, in a CRCS. From the mapped sampling points, a greater density of sampling points is generated 1216 in the CRCS reference. FIG. 10 shows, for example, the generating of the points 914 and 916 from sampling point 912 and the points 918 and 920 from sampling point 908. The generated density of sampling points, e.g., sampling points 908, 912, 914, 916, 918, and 920, is reverse mapped/correlated 1218 to matching data points within the VDS data of the RCS reference. Once having identified the relative motion needed to map the sampling points of the RCS to correlated sampling points in the CRCS, the identified relative motion is applied 1220 to the VDS data slices in the acquisition coordinate system to correct for motion artifacts in the VDS data. FIG. 11 illustrates an example whereby the identified relative motion is applied to slices 1102 of VDS data to obtain the motion corrected slices 1104.

Exemplary embodiments of diagnostic ultrasound systems are described above in detail. The systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method for correcting motion artifacts within a volumetric data set, comprising:
   obtaining a volumetric data set containing spatial and temporal information regarding an object, said volumetric data set being organized into data slices, at least two adjacent said data slices being representative of a common object at different points in time;
   determine relative motion between adjacent first and second data slices in said volumetric data set;
   correcting said relative motion between said adjacent first and second slices; and
   determining a cumulative motion of said first and second data slices with respect to a reference coordinate system of said volumetric data set.

2. The method of claim 1, wherein said determining includes calculating a difference in position and orientation between said first and second data slices as said relative motion.

3. The method of claim 1, further comprising repeating said determining and correcting for all of said data slices in said volumetric data set.

4. The method of claim 1, further comprising determining a corrected reference coordinate system for said first and second data slices, said corrected reference coordinate system differing from a coordinate system of said volumetric data set.

5. The method of claim 1, further comprising calculating a reference coordinate system based on said relative motion between said first and second data slices.

6. The method of claim 1, wherein said correcting includes mapping said first and second data slices into a new coordinate reference system, said first and second data slices, when mapped into said new coordinate reference system, being shifted with respect to one another based on said relative motion.

7. The method of claim 1, wherein said correcting includes rotating and translating at least one of said first and second data slices.

8. The method of claim 1, wherein said volumetric data set includes at least one of ultrasound, x-ray, CT, MR, and nuclear medicine data.

9. The method of claim 1, further comprising acquiring ultrasound data from the object, as said volumetric data set, continuously throughout a scan period, the object moving during said scan period at least through two cycles of a repeating pattern.

10. The method of claim 1, wherein said first and second data slices represent the common object at different first and second physical states.

11. The method of claim 1, wherein said first and second data slices represent different adjacent physical slices of the object.

12. A system for correcting motion artifacts within a volumetric data set, comprising:
   memory storing a volumetric data set containing spatial and temporal information regarding an object, said volumetric data set being organized into data slices, at least two adjacent said data slices being representative of a common object at different points in time; and
   a processing unit determine relative motion between adjacent first and second data slices in said volumetric data set, said processing unit, correcting said relative motion between said adjacent first and second slices, wherein said processing unit determines a cumulative motion of said first and second data slices with respect to a reference coordinate system of said volumetric data set.

13. The system of claim 12, wherein said processing unit calculates a difference in position and orientation between said first and second data slices as said relative motion.

14. The system of claim 12, wherein said processing unit repeats said determining and correcting operations for all of said data slices in said volumetric data set.

15. The system of claim 12, wherein said processing unit determines a corrected reference coordinate system for said first and second data slices, said corrected reference coordinate system differing from a coordinate system of said volumetric data set.

16. The system of claim 12, wherein said processing unit calculates a reference coordinate system based on said relative motion between said first and second data slices.

17. The system of claim 12, wherein said processing unit maps said first and second data slices into a new coordinate reference system, said first and second data slices, when mapped into said new coordinate reference system, being shifted with respect to one another based on said relative motion.

18. The system of claim 12, wherein said processing unit rotates and translates at least one of said first and second data slices when correcting said relative motion.

19. The system of claim 12, wherein said volumetric data set includes at least one of ultrasound, x-ray, CT, MR, and nuclear medicine data.

20. The system of claim 12, further comprising a probe acquiring ultrasound data from the object, as said volumetric data set, continuously throughout a scan period, the object moving during said scan period at least through two cycles of a repeating pattern.

21. The system of claim 12, wherein said first and second data slices represent the object at different first and second physical states.

22. The system of claim 12, wherein said first and second data slices represent different adjacent physical slices of the object.

* * * * *